United States Patent
Zander (12)

(10) Patent No.: US 6,194,138 B1
(45) Date of Patent: Feb. 27, 2001

(54) METHOD FOR FLUSHING BLOOD CELLS USING GELATIN

(76) Inventor: Rolf Zander, Luisenstrasse 17, D-55124 Mainz (DE)

( * ) Notice: Subject to any disclaimer, the term of this patent is extended or adjusted under 35 U.S.C. 154(b) by 0 days.

(21) Appl. No.: 09/134,581

(22) Filed: Aug. 14, 1998

(30) Foreign Application Priority Data

Aug. 16, 1997 (DE) .............................................. 197 35 460

(51) Int. Cl.⁷ .................................................... A01N 1/02
(52) U.S. Cl. ............................................................ 435/2
(58) Field of Search .................................................... 435/2

(56) References Cited

U.S. PATENT DOCUMENTS

| 3,970,427 | 7/1976 | Esposito et al. . |
| 5,554,527 | * 9/1996 | Fickenscher ....................... 435/240.1 |

FOREIGN PATENT DOCUMENTS

| 31 38 094 | 5/1982 | (DE) . |
| 39 38 907 | 5/1991 | (DE) . |
| 0 431 385 | 6/1991 | (EP) . |
| 93/14191 | 7/1993 | (WO) . |

OTHER PUBLICATIONS

Denning–Kendall et al., "Optimal processing of human umbilical cord blood for clinical banking", Experimental Hematology 24 : 1394–1401 (1996).*

Scholz et al., "Red cell aggregation induced by a high molecular weight gelatin plasma substitute", European Surgical Res. 3 (6) : 428–35 (1971).*

Seifen–Öle–Fette–Wachse, 116. Jg.–Nr. 16, p. 644 (1990).

Ganshirt, et al., "A Five–Bag System for Washing Fresh and Frozen Erythrocytes and their Preservation", Vox Sang. 26:66–73 (1974).

Brehme, et al., Hamorheologische Wirkungen von Hydroxyathylstarke 200/0,5, Dextran 40, Oxypolygelatine und Volleledtrolytlosung uber 48 Stunden, Innere Medizin 48, pp. 506–510 (1993).

Karger, et al., "The Significance of Quality of Whole Blood and Erythrocyte Concentration for Autologous Blood Transfusion", Anaesthesist 45: 694–707, Springer–Verlag (1996).

Finck, et al., "The Quality of Retransfused Red Cells", Anaesthesist, 35: 686–692, Springer–Verlag (1986).

Kummer, et al., "Separation of Platelet Rich Plasma and Red Cells with Modified Gelatin", Vox Sang, vol. 24, No. 1, pp. 76–88 (1973).

* cited by examiner

*Primary Examiner*—Sandra E. Saucier
(74) *Attorney, Agent, or Firm*—Michael L. Dunn

(57) ABSTRACT

An aqueous solution of gelatin used as a flushing liquid for blood cells, in particular erythrocytes, in order to give no changes in the blood cells or at most slight, quality-impairing changes.

18 Claims, No Drawings

METHOD FOR FLUSHING BLOOD CELLS USING GELATIN

BACKGROUND OF THE INVENTION

The invention concerns the field of flushing liquids for blood cells, in particular liquids for washing erythrocytes.

Flushing and storage liquids for blood cells, in particular for erythrocytes, are required in various processes. For example, in machine autotransfusion, that is to say obtaining and treating erythrocytes which are obtained intraoperatively, they are washed with a flushing liquid for subsequent retransfusion. In the machine treatment of blood components such as erythrocytes, leucocytes or thrombocytes, the cells are separated with a flushing liquid in so-called cell separators, so that they can be stored separately for a short period. The blood cells such as erythrocytes should be subjected to no changes or the minimum possible changes, by virtue of contact with such a liquid.

Nowadays the operation of flushing erythrocytes is usually implemented with physiological common salt solution. It is also known for so-called additive solutions such as for example mannitol, in the form of so-called SAG-mannitol or PAGGS-mannitol, to be added to erythrocyte concentrates to prolong the storage time (see Sibrowski, Anasthesiol. Intensivined. Notfallmed. Schmerzther. 1997, 32 (Suppl. 1), page 70). Gelatin-bearing infusion solutions are also known, but they have nothing to do with a use as flushing liquid for blood cells.

In regard to the washing of erythrocytes with NaCl-solution for autotransfusion it was found that the erythrocyte quality suffered from adverse effects due to the contact with the flushing liquid. Those erythrocyte quality losses are exhibited in particular due to impairment of the $O_2$-transport capability of the erythrocytes, which is characterised by the form and position of the so-called $O_2$-binding curve, by spontaneous haemolysis with the consequence of a rising haemoglobin and potassium concentration in the ambient liquid, by reduced 2,3-DPG- and ATP-content of the erythrocytes and disturbance in the acid-base housekeeping of the erythrocytes obtained. Quality losses of that kind are described in detail in the literature (see R. Karger, V. Kretschmer, Anaesthetist 1996, 45, pages 694–707; M. von Finck et al., Anaesthetist 1986, 35, pages 686–692). On the basis of present understanding in terms of the quality losses of erythrocytes their mechanical properties are in the forefront, with their consequences in regard to haemolysis and thus in regard to the loss of transfusable erythrocytes and the increase in extra-cellular free haemoglobin and potassium. The requirement accordingly is that erythrocyte preparations may only be transfused if haemolysis of the preparation is no greater than 0.8% (Council of Europe, Recommendations 1997).

It was in consideration of the quality impairments ascertained in respect of erythrocytes due to the contact with known flushing liquids that the object of the present invention arose, namely obtaining flushing liquids for blood cells, in particular erythrocytes, which do not involve any changes in the blood cells or at most slight changes such as to impair quality.

BRIEF DESCRIPTION OF THE INVENTION

It was surprisingly found that this object is achieved if, in accordance with the invention, an aqueous solution of gelatin is used as the flushing liquid for blood cells, in particular erythrocytes.

In accordance with the invention, a method is therefore provided for flushing erythrocytes including the steps of contacting the erythrocytes with an aqueous solution having a concentration of 25 to 100 g/l of gelatin having a molecular weight in the range of between 20,000 and 35,000 and adjusting the hematocrit by removal of excessive flushing liquid by centrifuging.

DETAILED DESCRIPTION OF THE INVENTION

As is known gelatin is a polypeptide which is obtained in particular by hydrolysis of the collagen contained in the skin and bones of animals. A wide molecular weight range is obtained in the production procedure. The polypeptide can be modified by reaction in particular of the amino groups with mono- or polyfunctional reagents such as for example with acylation agents, aldehydes, epoxides, halogen compounds, cyanamed or activated unsaturated compounds. Thus for example succinylated gelatin, oxypolygelatin and gelatin cross-linked by way of urea bridges are known in infusion solutions. Basically all modified or unmodified gelatin types can be employed for the use in accordance with the invention as flushing liquids.

Desirably the molecular weight of the gelatin used is so selected and the level of concentration of the gelatin in the aqueous solution is so adjusted and matched to the molecular weight that the aqueous solution obtained is substantially iso-oncotic, that is to say it substantially corresponds to the colloid-osmotic pressure of the plasma. In addition the matching of molecular weight and concentration of the gelatin is desirably such that the viscosity of the solution corresponds to the maximum possible degree to that of blood plasma and the density of the solution obtained is low. In that respect the gelatin is desirably so selected that its molecular weight is in the range of between 20,000 and 40,000, in particular in the range of between 30,000 and 35,000. Such gelatin types of unmodified or modified nature are commercially available. The level of concentration of the gelatin in the aqueous solution in accordance with the invention is desirably in the range of between 10 and 100 g/l, preferably in the range of between 25 and 60 g/l, particularly preferably in the range of between 30 and 55 g/l.

Depending on the respective purpose of use involved the aqueous solutions of gelatin which are used in accordance with the invention may contain conventional further constituents and can be sterilised and packaged in a sterile condition. Additional additives are for example agents for preventing blood coagulation such as citrate, heparin and heparin derivatives, glucose, in particular in an amount of between 2.5 and 7.5 mmol/l and electrolytes. They include in particular sodium, preferably in a concentration of between 130 and 150 mmol/l, potassium, preferably in a concentration of between 3 and 5 mmol/l, calcium, preferably in a concentration of between 1 and 3 mmol/l and magnesium, preferably in a concentration of between 0.5 and 1.5 mmol/l, in the aqueous gelatin solution.

EXAMPLES AND COMPARATIVE EXAMPLES

Aqueous solutions of four different commercially available gelatin types according to the invention as well as commercially available additives and dextrans and hydroxyethyl starch which are suitable for infusion solutions and finally physiological common salt solution were used for determining the haemolysis of erythrocytes. The solutions were compared in regard to spontaneous haemolysis and mechanical haemolysis, the gelatin solutions, hydroxyethyl starch solutions, dextran solutions and additive solutions being respectively brought together as their haemolysis values were in each case close together irrespective of the origin thereof.

Spontaneous haemolysis was ascertained as follows: fresh human blood was centrifuged three times (10 min at 1600 g), in each case with replacement of the plasma by excessive flushing liquid (10 ml of liquid per 2 ml erythrocytes). The haematocrit was adjusted to 50±5% by the removal of excessive flushing liquid. The concentration of the free haemoglobin in the last flushing liquid was then ascertained.

The mechanical haemolysis rate was ascertained by means of a tonometer IL 237 (from Instrumentation Laboratory). A thin, respectively fresh film of the erythrocytes was produced in that apparatus in a space which was temperature-controlled to 37° C. and through which flowed gases saturated with water vapour, in a glass vessel (volume a maximum of 8 ml), by intermittent rotation, that is to say by accelerating and stopping the vessel. Rotation was effected intermittently for one hour under physiological conditions (pH-value of 7.40 and $CO_2$-partial pressure of 40 mm Hg). The haemoglobin concentration in the supernatant matter was then determined. The values obtained are set out in the following Table.

TABLE

Spontaneous haemolysis (%) after suspension of erythrocytes and mechanical haemolysis rate (%/h) of erythrocytes (haematocrit 50 ± 5%)

|  | Spontaneous haemolysis (%) | Mechanical haemolysis rate (%/h) |
| --- | --- | --- |
| 7 plasma samples | not measurable | 0.06 ± 0.07 |
| 7 samples in 0.9 g/dl NaCl | 0.3 ± 0.2 | 2.2 ± 0.7 |
| Infusion solutions |  |  |
| 4 preparations of gelatin concentration 30–55 g/l MW 30,000–35,000 | 0.04 ± 0.04 | 0.1 ± 0.08 |
| 8 preparations hydroxyethyl starch concentration 30–100 g/l MW 70,000–450,000 | 0.3 ± 0.2 | 3.0 ± 0.7 |
| 7 preparations dextran concentration 60–100 g/l MW 40,000–70,000 | 0.4 ± 0.2 | 5.7 ± 2.7 |
| Additive solutions |  |  |
| 2 preparations PAGGS- or SAG-mannitol | 0.1 | 2.8 |

The values obtained show that both spontaneous haemolysis and also the mechanical haemolysis rate of the four gelatin solutions tested are comparable to the values of plasma and the gelatin solutions give negligible haemolysis. The values are far below the haemolysis value of 0.8% which is demanded by the Council of Europe. In contrast thereto the haemolysis values both for spontaneous haemolysis and also for mechanical haemolysis with the physiological common salt solution which is usually employed nowadays for the flushing of erythrocytes and the additive solutions which are usual nowadays for erythrocyte concentrate storage were considerably higher and far above the required value of 0.8%.

For comparative purposes known infusion solutions with hydroxyethyl starch and dextran were also included in the tests. Haemolysis with those polymers was even higher than with the investigated additive solutions and physiological common salt solution.

What is claimed is:

1. A method for flushing erythrocytes which comprises contacting the erythrocytes with an aqueous solution comprising gelatin wherein the gelatin in the solution is at a concentration of 25 to 100 g/l and the gelatin in the solution consists essentially of a molecular weight in the range of between 20,000 and 35,000 and adjusting the hematocrit by removal of excessive flushing liquid by centrifuging.

2. The method of claim 1, wherein the molecular weight and concentration of the gelatin are selected so that the solution is isooncotic.

3. The method of claim 2, wherein the concentration of gelatin is between about 25 and about 60 g/l.

4. The method of claim 3, wherein the solution contains an electrolyte selected from the group consisting of from about 130 to about 150 mmol/l sodium, from about 3 to about 5 mmol/l potassium, from about 1 to about 3 mmol/l of calcium, from about 0.5 to about 1.5 mmol/l of magnesium and mixtures thereof.

5. The method of claim 3, wherein the solution contains an anticoagulant.

6. The method of claim 2, wherein the solution contains from about 2.5 to about 7.5 mmol/l of glucose.

7. The method of claim 6, wherein the solution contains an electrolyte selected from the group consisting of from about 130 to about 150 mmol/l sodium, from about 3 to about 5 mmol/l potassium, from about 1 to about 3 mmol/l of calcium, from about 0.5 to about 1.5 mmol/l of magnesium and mixtures thereof.

8. The method of claim 7, wherein the solution contains an anticoagulant.

9. The method of claim 6, wherein the solution contains an anticoagulant.

10. The method of claim 2, wherein the solution contains an electrolyte selected from the group consisting of from about 130 to about 150 mmol/l sodium, from about 3 to about 5 mmol/l potassium, from about 1 to about 3 mmol/l of calcium, from about 0.5 to about 1.5 mmol/l of magnesium and mixtures thereof.

11. The method of claim 2, wherein the solution contains an anticoagulant.

12. The method of claim 1, wherein the molecular weight and concentration of the gelatin are selected so that the viscosity of the solution is about the same viscosity as blood plasma.

13. The method of claim 12, wherein the solution contains an electrolyte selected from the group consisting of from about 130 to about 150 mmol/l sodium, from about 3 to about 5 mmol/l potassium, from about 1 to about 3 mmol/l of calcium, from about 0.5 to about 1.5 mmol/l of magnesium and mixtures thereof.

14. The method of claim 1, wherein the concentration of gelatin is between about 25 and about 60 g/l.

15. The method of claim 14, wherein the concentration of gelatin is between about 30 and about 55 g/l.

16. The method of claim 1, wherein the solution contains from about 2.5 to about 7.5 mmol/l of glucose.

17. The method of claim 1, wherein the solution contains an electrolyte selected from the group consisting of from about 130 to about 150 mmol/l sodium, from about 3 to about 5 mmol/l potassium, from about 1 to about 3 mmol/l of calcium, from about 0.5 to about 1.5 mmol/l of magnesium and mixtures thereof.

18. The method of claim 1, wherein the solution contains an anticoagulant.

* * * * *